(12) United States Patent
Forbes et al.

(10) Patent No.: US 8,497,256 B2
(45) Date of Patent: Jul. 30, 2013

(54) FORMULATIONS AND USES OF 2-HYDROXY-5-PHENYLAZOBENZOIC ACID DERIVATIVES FOR THE TREATMENT OF MALES

(75) Inventors: William Forbes, Raleigh, NC (US); Enoch Bortey, Chapel Hill, NC (US); Lorin Johnson, Palo Alto, CA (US)

(73) Assignee: Salix Pharmaceuticals, Ltd, Raleigh, NC (US)

( * ) Notice: Subject to any disclaimer, the term of this patent is extended or adjusted under 35 U.S.C. 154(b) by 58 days.

(21) Appl. No.: 13/094,261

(22) Filed: Apr. 26, 2011

(65) Prior Publication Data
US 2012/0058184 A1    Mar. 8, 2012

Related U.S. Application Data

(60) Provisional application No. 61/328,151, filed on Apr. 26, 2010.

(51) Int. Cl.
 *A61K 31/355* (2006.01)
(52) U.S. Cl.
 USPC .............................. 514/149; 514/151; 514/158
(58) Field of Classification Search
 USPC .......................................... 514/149, 151, 158
 See application file for complete search history.

(56) References Cited

U.S. PATENT DOCUMENTS

| | | | |
|---|---|---|---|
| 4,298,595 A | | 11/1981 | Parkinson et al. |
| 2008/0096849 A1* | | 4/2008 | Johnson ........................ 514/150 |
| 2009/0252788 A1 | | 10/2009 | Lockhart et al. |
| 2010/0048519 A1 | | 2/2010 | Yeh et al. |

OTHER PUBLICATIONS

Alexander et al., American Disease Week and American Diabetes Association in Pharmacy and Therapeutics, 2008, 33(9), pp. 546-549.
Bottini et al. "Inflammatory bowel disease: Are there gender differences in the genetics of signal transduction? A preliminary study of cytosolic low molecular weight protein tyrosine phosphatase." Disease Markers 16(2000): 163-166.
Cosnes et al. 2004. "Gender differences in the response of colitis to smoking." Clinical Gastroenterology and Hepatology 2004; 2:41-48.
Hadziselimovic, F. et al. "Long-term 5-ASA treatment and gender-related differences in children with IBD," Autoimmune Diseases in Pediatric Gastroenterology, 2002, pp. 159-163, 127 Falk Symposium.
Hanauer, Dr. S.B. "Update on mesalazine for inflammatory bowel disease," Research and Clinical Forums, 1998, vol. 20, No. 1, pp. 203-208.
Schroeder, K.W., et al. "Coated Oral-5-Aminosalicylic Acid Therapy for Mildly to Moderately Active Ulcerative Colitis," N. Engl. J. Med., 1987, vol. 317, No. 26, pp. 1625-1629.

* cited by examiner

*Primary Examiner* — Benjamin Packard
(74) *Attorney, Agent, or Firm* — McCarter & English, LLP; Jonathan M. Sparks; Gabriel J. McCool

(57) ABSTRACT

The instant application provides methods and compositions for the treatment of male subjects having ulcerative colitis.

35 Claims, 3 Drawing Sheets

FORMULATIONS AND USES OF 2-HYDROXY-5-PHENYLAZOBENZOIC ACID DERIVATIVES FOR THE TREATMENT OF MALES

RELATED APPLICATIONS

This application claims priority to U.S. Provisional Appln. No. 61/328,151, filed on Apr. 26, 2010, which is incorporated in its entirety herein.

BACKGROUND OF THE INVENTION

Balsalazide disodium is indicated for the treatment of gastrointestinal diseases, for example mild to moderately active ulcerative colitis, radiation protosigmoidits, diverticulitis, irritable bowel syndrome (IBS) and colon cancer (see WO 95/18622). Balsalazide is a colon-specific, non-steroidal, anti-inflammatory aminosalicylate derivative. Balsalazide is also a prodrug containing 5-ASA, linked to 4-amino benzoyl-(3-alanine ("4-ABA") by a diazo bond.

SUMMARY OF THE INVENTION

This invention relates to the use of balsalazide to treat, prevent, or ameliorate gastrointestinal disorders in male subjects, e.g., mildly to moderately active ulcerative colitis (see, for example, Schroeder et al. (1987) N Engl J Med. 24; 317(26):1625-9).

More specifically, this invention relates to the use of balsalazide to treat male subjects having ulcerative colitis, irritable bowel syndrome and other non-inflammatory gastrointestinal (GI) conditions responding to mesalamine and balsalazide (see, for example, U.S. Pat. Nos. 326,364; 6,551,632; 6,475,518; 6,426,338; 6,277,836; 5,519,014; 5,476,669; 5,196,205 and 6,645,530, which are hereby incorporated by reference). The invention also relates to the use of balsalazide to treat gastrointestinal disease in male subjects, alone or in combination with other therapies.

The invention is due, in part, to the unexpected finding that administration of balsalazide is more effective for treating male subjects as compared to female subjects.

In one embodiment, the bioavailability of balsalazide is increased compared to administering balsalazide without food.

In one aspect, provided herein are methods for treating a gastrointestinal disorder comprising administering to a male subject in need of treatment a therapeutically effective amount of balsalazide. In one embodiment, the therapeutically effective amount comprises about 6.5 to about 6.8 g per day. In one embodiment, the therapeutically effective amount comprises about 6.6 g per day. In one embodiment, the therapeutically effective amount comprises about 6.75 g per day. In one embodiment, the therapeutically effective amount is a dosage regimen of three tablets of the formulation two times each day, wherein each tablet comprises about 1100 mg of balsalazide. In one embodiment, the balsalazide tablet is a film-coated tablet. In one embodiment, the therapeutically effective amount is a dosage regimen of three capsules of the formulation three times each day, wherein each capsule comprises about 750 mg of balsalazide. In one embodiment, the administration to the subject occurs between about 30 minutes prior to about 1 hour after consuming food. In one embodiment, the gastrointestinal disorder comprises ulcerative colitis. In one embodiment, the ulcerative colitis is mild to moderately active ulcerative colitis.

In one aspect, provided herein are methods of decreasing a MMDAI score in a male subject having ulcerative colitis comprising administering to the subject a therapeutically effective amount of balsalazide, thereby decreasing the MMDAI score. In one embodiment, the therapeutically effective amount comprises between about 6.5 to about 6.8 g per day. In one embodiment, the therapeutically effective amount comprises about 6.6 g per day. In one embodiment, the therapeutically effective amount comprises about 6.75 g per day. In one embodiment, the therapeutically effective amount is a dosage regimen of three tablets of the formulation two times each day, wherein each tablet comprises about 1100 mg of balsalazide. In one embodiment, the balsalazide tablet is a film-coated tablet. In one embodiment, the therapeutically effective amount is a dosage regimen of three capsules of the formulation three times each day, wherein each capsule comprises about 750 mg of balsalazide. In one embodiment, the MMDAI score is decreased by 3 or more points. In one embodiment, the rectal bleeding component of the MMDAI score is decreased by 1 or more points.

In one aspect, provided herein are methods of inducing clinical remission of ulcerative colitis in a male subject comprising; administering to the subject a therapeutically effective amount of balsalazide, thereby inducing remission in the subject. In one embodiment, the therapeutically effective amount comprises between about 6.5 to about 6.8 g per day. In one embodiment, the therapeutically effective amount comprises about 6.6 g per day. In one embodiment, the therapeutically effective amount comprises about 6.75 g per day. In one embodiment, the therapeutically effective amount is a dosage regimen of three tablets of the formulation two times each day, wherein each tablet comprises about 1100 mg of balsalazide. In one embodiment, the balsalazide tablet is a film-coated tablet. In one embodiment, the therapeutically effective amount is a dosage regimen of three capsules of the formulation three times each day, wherein each capsule comprises about 750 mg of balsalazide. In one embodiment, remission is defined by MMDAI component scores of zero for rectal bleeding and a combined score of 2 or less for bowel frequency and physician's assessment.

In one aspect, provided herein are methods of inducing mucosal healing in a male subject having ulcerative colitis comprising administering to the subject a therapeutically effective amount of balsalazide, thereby inducing mucosal healing in the subject. In one embodiment, the therapeutically effective amount comprises between about 6.5 to about 6.8 g per day. In one embodiment, the therapeutically effective amount comprises about 6.6 g per day. In one embodiment, the therapeutically effective amount comprises about 6.75 g per day. In one embodiment, the therapeutically effective amount is a dosage regimen of three tablets of the formulation two times each day, wherein each tablet comprises about 1100 mg of balsalazide. In one embodiment, the balsalazide tablet is a film-coated tablet. In one embodiment, the therapeutically effective amount is a dosage regimen of three capsules of the formulation three times each day, wherein each capsule comprises about 750 mg of balsalazide. In one embodiment, the mucosal healing is defined as an improvement in endoscopy/sigmoidoscopy score to 0 or 1.

Other embodiments of the invention are disclosed infra.

DETAILED DESCRIPTION OF THE FIGURES

Figure 1:
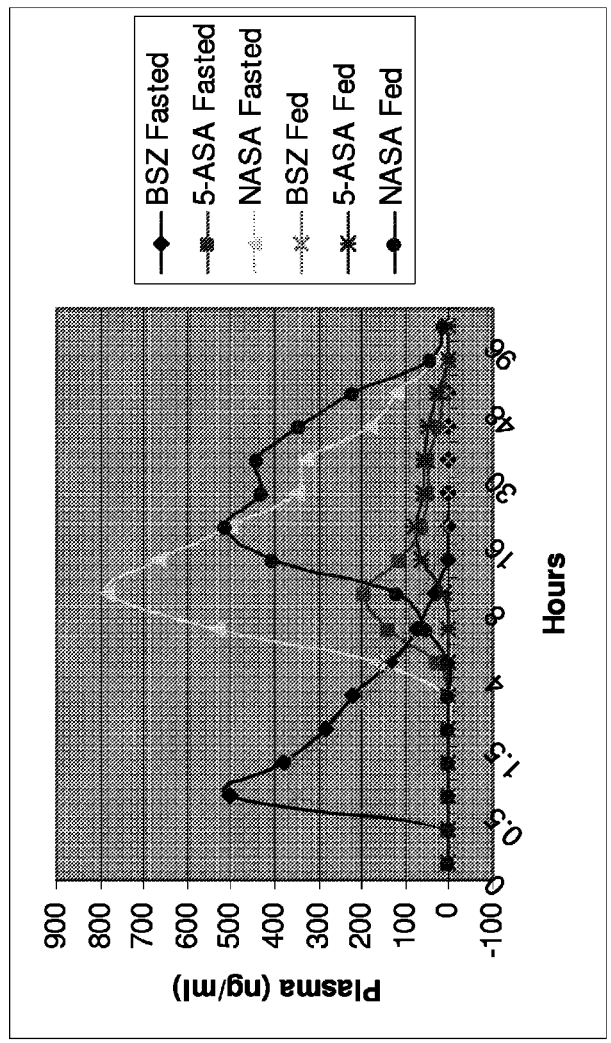
FIG. 1 shows plasma levels of balsalazide and metabolites in fed and fasted states.
Figure 2:
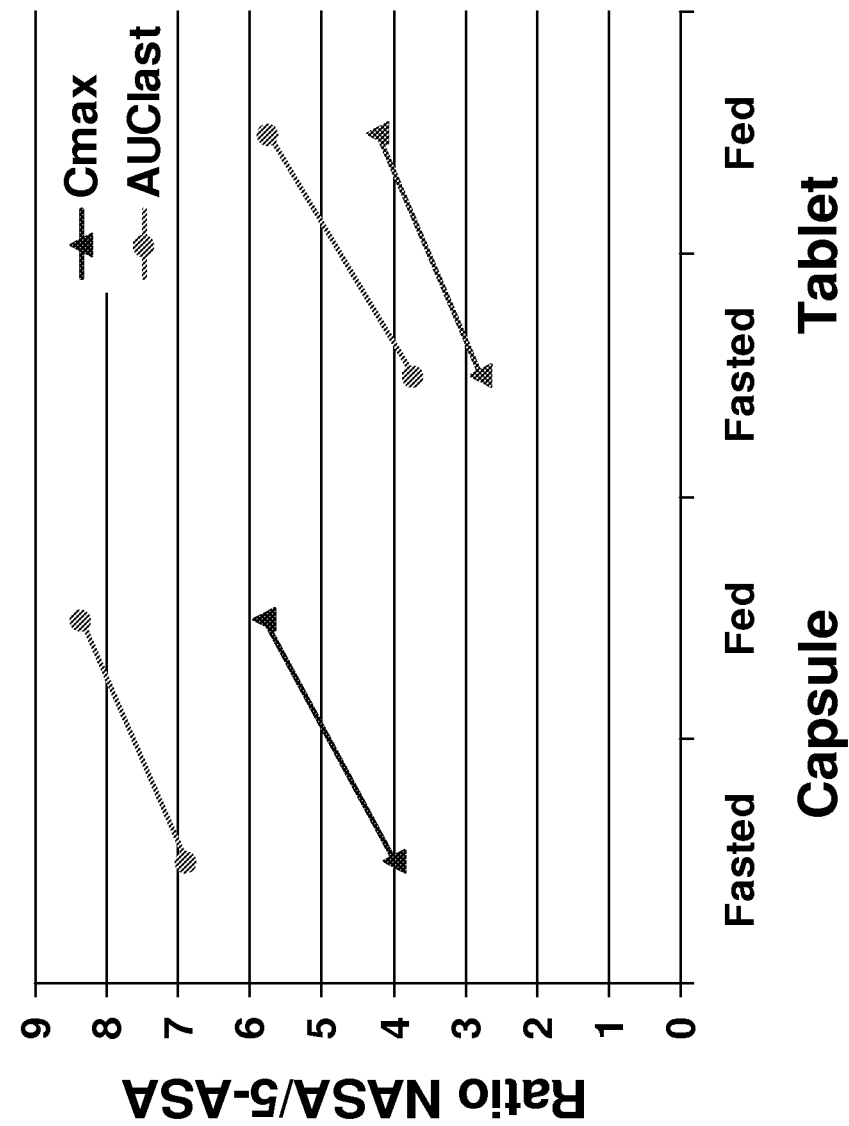
FIG. 2 shows the ratios of NASA/5-ASA of the capsules and tablets of balsalazide in the fed and fasted states.
Figure 3:
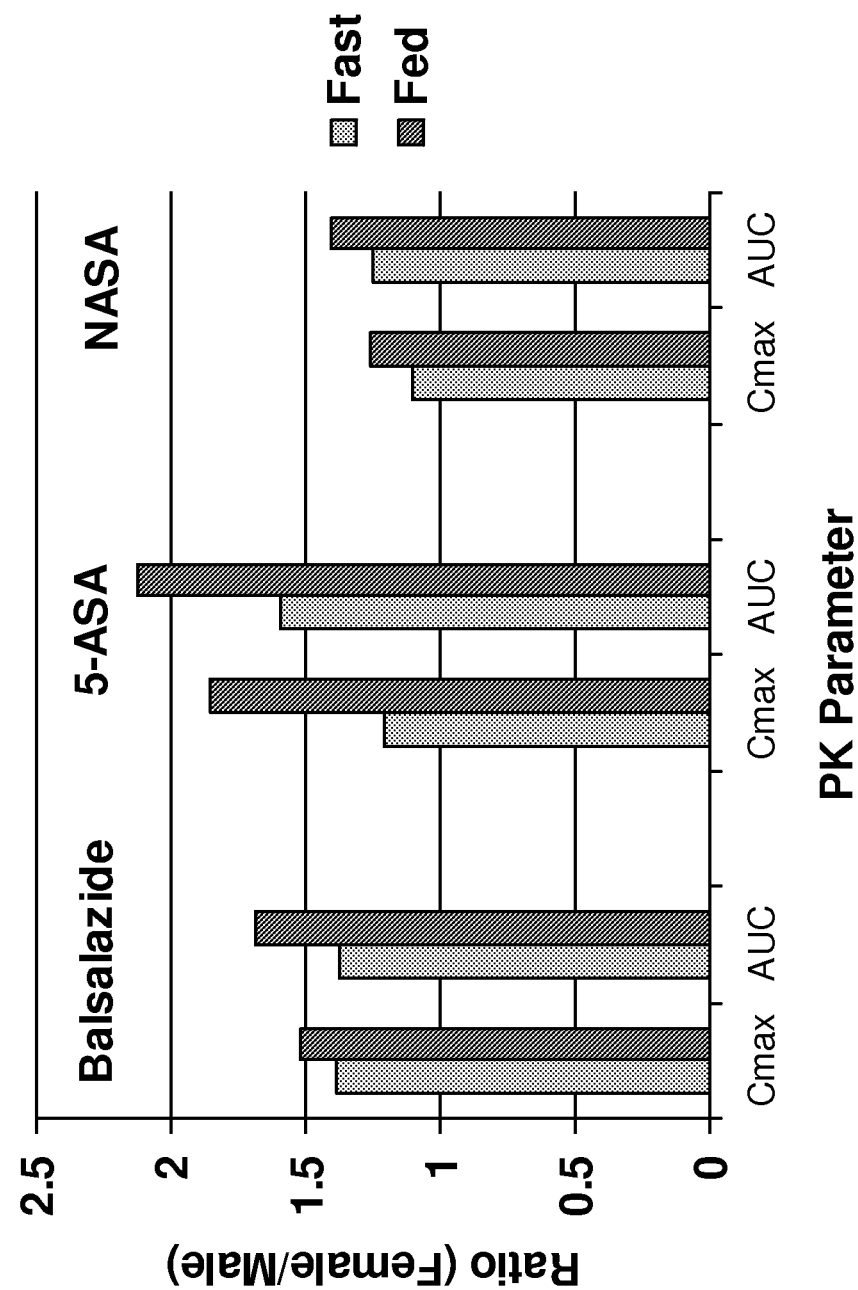

FIG. 3 presents the balsalazide, 5-ASA and NASA plasma levels as a ratio of the female levels divided by the male levels. A value of 1.0 in the graph would be indicative of equal absorption in both sexes.

DETAILED DESCRIPTION

Disclosed herein are compositions and methods of treating gastrointestinal disorders in male subjects by administering balsalazide. In one embodiment, the balsalazide can be administered in the form of a film-coated tablet containing 1.1 g balsalazide or for example as 750 mg capsules. For example, an adult male dose is three 750 mg capsules of balsalazide administered 3 times a day (6.75 g/day) with or without food for 8 weeks.

Before further description and in order that the invention may be more readily understood, certain terms are first defined and collected here for convenience. Common pharmacologic term used herein refer are as follows: $T_{max}$ (time to maximum concentration); $C_{max}$ (observed maximum concentration); kel (slope of terminal linear portion of concentration/time curve); $T_{1/2}$ (half-life of balsalazide calculated as: 0.693/Kel); $AUC_{(last)}$ (area under the curve to last quantifiable concentration as measured by the trapezoidal rule); and $AUC_{(inf)}$ (the AUC value extrapolated to infinity calculated as: $AUC_{(inf)} = AUC_{(last)} + C_{(t)last}/Kel$ where $C_{(t)}$ last is the last measurable concentration).

The term "administration" or "administering" includes routes of introducing balsalazide to a subject to perform their intended function. The pharmaceutical preparations may be given by forms suitable for each administration route. Oral administration is preferred. Depending on the route of administration, balsalazide can be coated with or disposed in a selected material to protect it from natural conditions that may detrimentally affect its ability to perform its intended function. Balsalazide can be administered alone, or in conjunction with either another agent or agents as described herein or with a pharmaceutically-acceptable carrier, or both. Balsalazide can be administered prior to the administration of the other agent, simultaneously with the agent, or after the administration of the agent.

"Chemotherapy," as used herein, includes therapies administered systemically for the treatment of neoplastic disease processes (commonly cancer), and may include, for example, biological therapies such as small molecule inhibitors, monoclonal antibodies (e.g., Iressa, Tarceva, Erbitux), or other biological agents administered with a similar objective which may result in symptoms such as those herein described, e.g., inflammation of the intestine, those causing a disproportionate incidence of diarrhea or an increased risk of diarrhea.

The term "effective amount" includes an amount effective, at dosages and for periods of time necessary, to achieve the desired result, e.g., sufficient to treat or prevent an inflammatory bowel disease. An effective amount of balsalazide may vary according to factors such as the disease state, age, and weight of the subject, and the ability of balsalazide to elicit a desired response in the subject. Dosage regimens may be adjusted to provide the optimum therapeutic response. An effective amount is also one in which any side effects of balsalazide are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with balsalazide, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of enteritis or diarrhea within a subject. Amelioration may be transient, prolonged or permanent or it may be variable at relevant times during or after balsalazide is administered to a subject or is used in an assay or other method described herein or a cited reference, e.g., within timeframes described infra, or about 1 hour after the administration or use of balsalazide to about 3, 6, 9 months or more after a subject(s) has received balsalazide.

As used herein, "administered with food" refers to, for example, any food product, solid or liquid, with caloric content. Preferably the food is a solid food with sufficient bulk and fat content that it is not rapidly dissolved and absorbed in the stomach. More preferably the food is a meal, such as breakfast, lunch or dinner. The dosage of balsalazide may be administered to the subject, for example, between about 30 minutes prior to about 2 hours after eating a meal, most advantageously the dosage is administered within 15 minutes of eating a meal. The terms "without food", "fasted" and "an empty stomach" refer to, for example, the condition of not having consumed solid food for about 1 hour prior to until about 2 hours after such consumption.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with balsalazide, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after balsalazide is administered to a subject or is used in an assay or other method described herein or a cited reference, e.g., within times descried infra, or about 1 hour of the administration or use of balsalazide to about 3, 6, 9 months or more after a subject(s) has received balsalazide. The term "modulate" may also refer to increases or decreases in the activity of a cell in response to exposure to a balsalazide, e.g., the inhibition of proliferation and/or induction of differentiation of at least a sub-population of cells in an animal such that a desired end result is achieved, e.g., a therapeutic result of balsalazide used for treatment may increase or decrease over the course of a particular treatment.

The term "obtaining" as in "obtaining balsalazide" is intended to include purchasing, synthesizing or otherwise acquiring balsalazide.

As used herein, the term "prophylactically effective amount" refers to the amount of a therapy (e.g., a composition comprising balsalazide) which is sufficient to result in the prevention of the development, recurrence, or onset of enteritis and/or diarrhea or one or more symptoms thereof, or to enhance or improve the prophylactic effect(s) of another therapy. In one embodiment, the language "a prophylactically effective amount" of a compound refers to an amount of balsalazide which is effective, upon single or multiple dose administration to the subject, in preventing or treating, for example, colitis, Crohn's disease, diverticulits, irritable bowel syndrome (IBS), enteritis and/or diarrhea.

The phrases "systemic administration," "administered systemically," "peripheral administration," and "administered peripherally," as used herein mean the administration of balsalazide, drug or other material, such that it enters the subject's system and, thus, is subject to metabolism and other like processes, for example, subcutaneous administration.

The language "therapeutically effective amount" of balsalazide refers to an amount of balsalazide which is effective, upon single or multiple dose administration to the subject, in inhibiting the bacterial growth and/or invasion, or in decreasing symptoms of bacterial infection in a subject with such a bacterial infection sooner that expected in the absence of such treatment. "Therapeutically effective amount" also refers to the amount of a therapy (e.g., a composition comprising balsalazide), which is sufficient to reduce the severity of enteritis and/or diarrhea, reduce the duration of enteritis and/or diarrhea, prevent the advancement of enteritis and/or diarrhea, cause regression of enteritis and/or diarrhea, ameliorate one or more symptoms associated with enteritis and/or diarrhea, or enhance, facilitate, or improve the therapeutic effect(s) of another therapy.

As used herein, the terms "prevent," "preventing," and "prevention" refer to the prevention of the recurrence, onset, or development of colitis (including, ulcerative, active, moderate, mild or severe colitis), enteritis and/or diarrhea or one or more symptoms thereof in a subject resulting from the administration of an abdominopelvic therapy or from travel. Preventing includes protecting against radiation induced enteritis, protecting against radiation induced injury to the mucosa of the colon, protecting against radiation induced colorectal inflammation, and/or radiation-induced inflammation or bacterial invasion of other portions of the alimentary tract. For example, balsalazide may be formulated as a mouthwash to treat or ameliorate radiation-induced esophagitis or other radiation-induced mucositis. For example, balsalazide may be given to a traveler prior to travel to reduce or prevent enteritis or diarrhea.

As used herein, the terms "subject" and "subjects" includes male organisms which are capable of suffering from a gastrointestinal disease, e.g., colitis, e.g., ulcerative colitis, e.g., mild, moderate or severe, or who could otherwise benefit from the administration of a balsalazide and refer to an animal, preferably a mammal, including a non-primate (e.g., a cow, pig, horse, cat, or dog), a primate (e.g., a monkey, chimpanzee, or human), and more preferably a human male.

Susceptible to gastrointestinal diseases, e.g., enteritis, diarrhea, colon cancer, ulcerative colitis, is meant to include subjects at risk of developing the gastrointestinal diseases, and the like, and subjects who have suffered from colitis in the past, subjects having a family history of colitis or cancer and the like.

As used herein, the terms "treat," "treatment," and "treating" refer to the reduction of the progression, severity, and/or duration of colitis, enteritis and/or diarrhea or amelioration of one or more symptoms thereof, wherein such reduction and/or amelioration result from the administration of one or more therapies (e.g., a composition comprising balsalazide).

In some embodiments, "clinical improvement" is defined as having both a $\geq 3$ point improvement from baseline in the MMDAI score and a $\geq 1$ point improvement from baseline in the rectal bleeding subscore. In some embodiments, "clinical remission" is defined as a score of 0 for rectal bleeding and a combined score of $\leq 2$ for bowel frequency and physician's assessment using the MMDAI subscale. In some embodiments, "mucosal healing" is defined as an endoscopy/sigmoidoscopy score of 0 or 1, where a score of 1 includes signs of erythema or decreased vascular pattern; by definition, the presence of friability indicates a score of 2 or 3.

The phrase "pharmaceutically acceptable" refers to compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Determining a subject in need thereof may be by one or more of colonoscopy, symptom analysis, or medical assessment and other methods described infra.

Balsalazide and Pharmaceutical Compositions

Balsalazide is a prodrug of mesalamine (5-aminosalicylic acid, 5-ASA). The mechanism of action of 5-ASA is unknown, but appears to be local to the colonic mucosa rather than systemic. Mucosal production of arachidonic acid metabolites, both through the cyclooxygenase pathways, i.e., prostanoids, and through the lipoxygenase pathways, i.e., leukotrienes and hydroxyeicosatetraenoic acids, is increased in patients with ulcerative colitis, and it is possible that 5-ASA diminishes inflammation by blocking production of arachidonic acid metabolites in the colon.

Balsalazide disodium is a a prodrug that is enzymatically cleaved to produce mesalamine (5-aminosalicylic acid, 5-ASA), an anti-inflammatory drug. It is a stable, odorless, orange to yellow, microcrystalline powder. It is freely soluble in water and isotonic saline, sparingly soluble in methanol and ethanol, and practically insoluble in all other organic solvents. Balsalazide disodium has the chemical name (E)-5-[[-4-[[(2-carboxyethyl) amino]carbonyl]phenyl]azo]-2-hydroxybenzoic acid, disodium salt, dihydrate (Molecular Weight: 437.32; Molecular Formula: $C_{17}H_{13}N_3O_6Na_2.2H_2O$).

Balsalazide is the generic name for GIAZO®. Examples of uses and manufacture of balsalazide may be found, for example in U.S. Pat. Nos. 6,197,341; 5,905,073; 5,498,608; and 6,326,364; which are hereby incorporated by reference in their entirety. Balsalazide is useful in the methods described herein to increase their bioavailability and efficacy Each GIAZO tablet contains 1.1 g of balsalazide disodium, film-coated for oral delivery. Balsalazide disodium is insoluble in acid, but soluble at a pH of at least 4.5. Inactive ingredients comprise hypromellose, magnesium stearate, and Opadry II Yellow. The sodium content of each tablet is approximately 126 mg.

Following oral administration, balsalazide is cleaved by azoreductases produced by anaerobic bacteria, found in the gut, to release equimolar quantities of 5-ASA, the active moiety, and 4-aminobenzoyl-β-alanine (4-ABA), a carrier moiety. Both of these moieties are N-acetylated to form N-Ac-5-ASA and N-Ac-4-ABA, respectively.

The released 4-ABA carrier component is poorly absorbed and largely eliminated in the feces (Ragunath K and Williams J G. Aliment Pharmcol. Ther. 2001; 15:1549-1554). The local presence of 5-ASA is the basis for the effectiveness of this class of drugs and mucosal 5-ASA concentrations are correlated inversely with UC disease activity (Frieri G, Giacomelli R, Pimpo M. et al. Gut 2000; 47:410-414). While the actual mechanism of action of 5-ASA is not completely understood, systemic exposure of 5-ASA is thought to be responsible for the sides effects associated with treatment. Most prevalent in studies on balsalazide is headache (Green J B Gastroenterology 1999; 117:1513-1514) and lower systemic levels of 5-ASA may contribute to a lower incidence of headache as observed in some trials (Levine D S, Riff D S, Pruitt R et al. Am. J. Gastroenterol. 2002; 9:1398-1407). Dose regimens that increase the local mucosal concentration of the active therapeutic moiety and decrease the systemic absorption of 5-ASA are therefore preferred.

While 5-ASA is the active therapeutic moiety of balsalazide, it is rapidly converted to the metabolite N-acetyl-5-ASA (5-Ac-5-ASA; NASA) in the mucosa (Allgayer H, Ahnfelt N O, Kruis W et al Gastroenterology. 1989; 97:38-41). Approximately, 12% of the oral dose can be measured in the blood as this metabolite as compared to <2% of the oral dose of 5-ASA that is systemically absorbed (van Hogezand R A, van Hees P A, van Gorp J P, van Lier H J, Bakker J H, Double-blind comparison of 5-aminosalicylic acid and acetyl-5-aminosalicylic acid suppositories in subjects with idiopathic proctitis Aliment Pharmacol Ther. 1988 February; 2(1):33-40).

It has surprisingly been found that the administration of balsalazide to a male subject experiencing ulcerative colitis, e.g., mildly to moderately active ulcerative colitis, reduces symptoms of the condition. Balsalazide is the generic name for a 2-hydroxy-5-phenylazobenzoic acid derivative in which an aminosalicylate moiety, 5-aminosalicylic acid (5-ASA) (mesalamine), is linked to a carrier molecule, 4-aminobenzoyl-β-alanine (4-ABA), through an azo-bond. Disodium balsalazide is highly water-soluble and is cleaved in the colon to release mesalamine, which is the therapeutically active portion of the molecule, as well as 4-aminobenzol-β-alanine, which is the carrier moiety. Mesalamine is 5-aminosaliacylic acid and appears to act topically.

One mechanism for the surprising observation of a increased efficacy in males to balsalazide is the finding that that female subjects display greater absorption of balsalazide and its metabolites, 5-ASA and N-acetyl-5-ASA (NASA) in the blood, e.g., systemic bioavailability. Balsalazide and its metabolites work topically in the colon, e.g., colonic bioavailability, to treat the underlying pathology, the greater absorption into the blood compartment would mean a lowering of their level in the colon and less colonic bioavailability. This observation is shown in FIG. 3, where the balsalazide, 5-ASA and NASA plasma levels are presented as a ratio of the female levels divided by the male levels. Thus, a value of 1.0 in the graph would be indicative of equal absorption in both sexes. As is evident from FIG. 3, the female subjects consistently display greater plasma levels relative to the male subjects. These range from 10-60% greater in the fasted state to 25-120% greater in the fed state.

The use of balsalazide to treat gastrointestinal disorders is especially beneficial because balsalazide is metabolized by intestinal microflora to the active form, 5-ASA, thus ensuring delivery of the active drug to the bowel without loss via absorption more proximally in the intestinal tract. Balsalazide also exhibits fewer side effects than other 5-ASA prodrugs and it may be administered to subjects with sulpha allergies. Balsalazide is also beneficial because the active component has been demonstrated to directly scavenge free radicals, which may reduce subsequent inflammatory response. Dosages, according to certain preferred embodiments, range from between about 6.0 mg to about 14000 mg of balsalazide administered daily. For example, a dose is three 1.1 g balsalazide tablets may be taken 2 times a day for a total of 6.6 g per day. Other appropriate dosages for methods according to this invention may be determined by health care professionals or by the subject. The amount of balsalazide administered daily may be increased or decreased based on the weight, age, health, sex or medical condition of the subject. One of skill in the art would be able to determine the proper dose for a subject based on this disclosure.

Methods of Treatment

Described herein are methods of treating male subjects suffering from or susceptible to gastrointestinal disorders by administering balsalazide to a subject.

According to one aspect, provided herein are methods for treating a male subject having or susceptible to developing a gastrointestinal disorder, e.g., ulcerative colitis, comprising administering to the male subject a therapeutically effective amount of balsalazide.

Therapeutically effective amounts, according to the methods described herein include doses of about 6.0 g/day to about 7 g/day, for example, as tablets or capsules. Therapeutically effective amounts and dosage regimens include, administering three tablets or capsules of the formulation once, twice or three two times each day, wherein each tablet or capsule comprises from about 750 mg to about 1100 mg of balsalazide. For example, a therapeutically effective amount of balsalazide may be administration of three 750 mg capsules three times a day (6.75 g/day). A more preferred administration to males comprises administration of three 1.1 g tablets two times a day.

The administration to the subject can occur, for example, between about 30 minutes prior to about 2 hours after consuming food. The administration with food may also be at the same time as the consumption of the food. Also, the administration to the subject may be, for example, immediately after the consumption of food up to about 1 hour after the consumption. The food may comprise, for example, applesauce or a high-fat meal.

According to one aspect, provided herein are methods of decreasing the modified Mayo Disease Activity Index (MMDAI) score of a male subject having ulcerative colitis by administering a therapeutically effective amount of balsalazide to the subject. In one embodiment, the MMDAI score is decreased by three or more points or the rectal bleeding component of the MMDAI score is decreased by one or more points. The modified Mayo Disease Activity Index (MMDAI) is a sum of four subscores (bowel frequency, rectal bleeding, endoscopic appearance, and physician's global assessment), each ranging from 0 to 3, with higher scores indicating worse disease. See for example, Schroeder et al. (1987) N Engl J Med. 24; 317(26):1625-9.

According to one aspect, provided herein are methods of inducing clinical remission of ulcerative colitis in male subjects. In one embodiment, remission is defined as an MMDAI component score of 0 for rectal bleeding and a combined score of two or less for the MMDAI components of bowel frequency and physician's assessment.

According to one aspect, provided herein are methods of inducing mucosal healing in male subjects having ulcerative colitis. In one embodiment, mucosal healing is determined by an improvement in the endoscopy/sigmoidoscopy score of 0 to 1.

In one embodiment, the balsalazide is from a container comprising labeling advising that balsalazide should be administered with food.

According to one aspect, a method of treating a subject suffering from a gastrointestinal disease, e.g., mild to moderately active ulcerative colitis, comprises administering to the subject a therapeutically effective amount of balsalazide. In one embodiment, balsalazide is sodium balsalazide dihydrate. In one embodiment, the pharmaceutical composition is administered orally to an individual suffering from or at risk to develop a gastrointestinal disorder in a daily dosage range of about 6 to about 7 grams per day, e.g., 6.6 g.

In another embodiment, the gastrointestinal disease is mild to moderately active ulcerative colitis.

Yet another aspect of this invention relates to a method of treating a male subject with balsalazide who is in need thereof. Identifying a subject in need of such treatment can be in the judgment of a subject or a health care professional and can be subjective (e.g., opinion) or objective (e.g., measurable by a test or diagnostic method).

Balsalazide may be administered prior to, during, and/or after the treatment therapies or travel or exposure to other at risk conditions. Balsalazide may be administered, for example, once a day, twice a day, three times a day, or four times a day. Balsalazide may be administered in doses, for example of about 6.6 g/day. Balsalazide may be administered, for example, in tablet form, powered form, liquid for or in capsules. Balsalazide tablets may be film-covered tablets marketed under the brand name GIAZO®.

In certain embodiments, balsalazide is administered to a male subject from between about 2 weeks to about 6 weeks in duration, from between about 8 weeks to about 12 weeks in duration, or from between 1 day to about 7 days. Balsalazide may be administered intermittently or continuously during the course of treatment.

For any of the embodiments, balsalazide may be administered, for example, once daily, twice daily, three times daily, or four times daily to a subject. In some particularly preferred methods of the present invention comprise administering balsalazide twice daily to the subject because it may, for example, minimize the side effects and increase subject compliance.

Dosages, according to certain preferred embodiments, are about 6.6 g of balsalazide administered daily. Other appropriate dosages for methods according to this invention may be determined by health care professionals or by the subject. The amount of balsalazide administered daily may be increased or decreased based on the weight, age, health, sex or medical condition of the subject. One of skill in the art would be able to determine the proper dose for a subject based on this disclosure.

In certain embodiments, one or more formulations and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, e.g., the cycle in order to reduce the development of resistance to one of the therapies, to avoid or reduce the side effects of one of the therapies, and/or to improve the efficacy of the therapies.

In certain embodiments, the administration of the same formulations of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a gastro-resistant balsalazide formulation may be repeated and the administration may be separated by at least at least 1 day, 2 days, 3 days, 5 days, 10 days, 15 days, 30 days, 45 days, 2 months, 75 days, 3 months, or at least 6 months.

Certain indications may require longer treatment times. Short-term treatments include, for example, treatment for 1 to about 7 days. Long-term treatments with balsalazide, include for example, treatment for 15 days, 3 months, 9 months, 7 days/month for three months, 7 days/month for three to twelve months or any time in-between or longer. One of skill in the art, having the benefit of this disclosure would understand how to vary the dosage for a particular subject or intended result. Dosage regimens will vary depending on the age, size, and condition of the subject. For example, depending on the severity of the disease, or injury whether it is a new disease state or a relapse or recurrence, etc.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The total daily dosage of balsalazide formulations, for example of balsalazide, can be about 6.6 g. For example, in general, the total daily adult dosage of balsalazide in formulations of the present invention ranges from about 6000 mg to about 7000 mg, about, about 6200 to about 6800 mg, or any whole number or fractional amount in between. In one embodiment, a single dose contains about 1100 mg of balsalazide.

Balsalazide may be provided as a film-coated tablet formulation.

Balsalazide formulations may be of any polymorphic or amorphous form of balsalazide.

In an embodiment, balsalazide is administered to the subject using a pharmaceutically-acceptable formulation, e.g., a pharmaceutically-acceptable formulation that provides sustained delivery of balsalazide to a subject for at least 12 hours, 24 hours, 36 hours, 48 hours, one week, two weeks, three weeks, or four weeks after the pharmaceutically-acceptable formulation is administered to the subject.

In some embodiments, it may be desirable to administer the pharmaceutical compositions of the invention locally to the area in need of treatment. This may be achieved by, for example, local infusion during surgery, or topical application, e.g., in conjunction with a wound dressing after surgery, by injection, by means of a catheter, by means of a suppository, or by means of an implant (the implant being of a porous, non-porous, or gelatinous material, including membranes, such as sialastic membranes, or fibers). In one embodiment, administration can be by direct injection at the site, e.g., enema. In another embodiment, balsalazide can be formulated in a viscous or non-viscous solution for oral administration. In a separate embodiment, balsalazide can be formulated in a viscous or non-viscous mixture containing a pain reliever, e.g., lidocaine.

In certain embodiments, these pharmaceutical compositions of balsalazide are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; topical application, for example, as a cream, ointment or spray applied to the gastrointestinal tract; intrarectally, for example, as a pessary, cream or foam; or aerosol, for example, as an aqueous aerosol, liposomal preparation or solid particles containing the compound.

The phrase "pharmaceutically acceptable" refers to compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

It is advantageous to administer balsalazide to males because less of the molecule and metabolites are absorbed systemically leaving more in the colon for local colonic bioavailability. For example, see FIG. 3, which shows that with or without food, less of the balsalazide and metabolites are systemically absorbed in the men taking the compound. This was previously an unappreciated aspect of administering balsalazide and it was surprising to find that administration to males has increased efficacy as compared to females.

Article of Manufacture

The article of manufacture comprises, for example, a container holding a film-coated pharmaceutical composition or a capsule or a combination of the two suitable for oral administration of balsalazide in combination with printed labeling instructions providing a discussion of when a particular dosage form should be administered to male subjects. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect of this invention is an article of manufacture that comprises a container containing a pharmaceutical composition comprising balsalazide wherein the container holds preferably balsalazide composition in unit dosage form and is associated with printed labeling instructions advising of efficacy of the pharmaceutical composition when administered to male subjects.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing balsalazide include, for example, those suitable for oral, nasal, topical (including buccal and sublingual), rectal, vaginal, aerosol percutaneous, and/or parenteral administration. For instance, to treat an infected external biliary drain, balsalazide could be administered percutaneously via that drain, thus resulting in an "intrabiliary" administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, more preferably from about 10% to about 30% active ingredient.

Methods of preparing these balsalazide compositions include the step of bringing into association balsalazide with the carrier and, optionally, one or more accessory ingredients. In general, the formulations are prepared by uniformly and intimately bringing into association with balsalazide with liquid carriers, or finely divided solid carriers, or both, and then, if necessary, shaping and coating the product.

Balsalazide compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-inwater or water-in-oil liquid emulsion, or as an elixir or syrup, or as pastilles (using an inert base, such as gelatin and glycerin, or sucrose and acacia) and/or as mouth washes and the like, each containing a predetermined amount of balsalazide as an active ingredient. A compound may also be administered as a bolus, electuary or paste.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as film coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of balsalazide include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Pharmaceutical compositions of the invention for rectal administration may be presented as a suppository, which may be prepared by mixing balsalazide with one or more suitable nonirritating excipients or carriers comprising, for example, cocoa butter, polyethylene glycol, a suppository wax or a salicylate, and which is solid at room temperature, but liquid at body temperature and, therefore, will melt in the rectum and release the active agent.

Dosage forms for the topical or transdermal administration of balsalazide include powders, sprays, ointments, pastes, creams, lotions, gels, solutions, patches and inhalants. Balsalazide may be mixed under sterile conditions with a pharmaceutically-acceptable carrier, and with any preservatives, buffers, or propellants which may be required.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution that in turn may depend upon crystal size and crystalline form. Alternatively, delayed absorption of a parenterally-administered drug form is accomplished by dissolving or suspending the drug in an oil vehicle.

Injectable depot forms are made by forming microencapsule matrices of balsalazide in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When balsalazide are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

In some cases, to ameliorate, for example, simultaneously, conditions associated with the condition for which balsalazide is administered, such as pain, candida, dysphagia, odynophagia, mucositis, esophagitis, pneumonitis, stomatitis, or xerostomia, balsalazide may be formulated as a combination with other appropriate agents including but not limited to nystatin, ketoconazole, fluconazole, lidocaine, benzocaine, diphenhydramine, dimenhydrinate, azelastine, cetirizine, hydrocortisone, prednisone, prednisolone, dexamethasone, triamcinolone, beclomethosone, budesonide, mometasone, or other steroid, local anesthetic, anti-fungal, or antihistamine agents. This formulation may take the form of a viscous or non-viscous liquid, a topically applied compound, an aerosol, or an injectable.

Regardless of the route of administration selected, balsalazide, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular subject, composition, and mode of administration, without being toxic to the subject. Exemplary dosage forms are disclosed infra.

Packaged compositions are also provided, and may comprise a therapeutically effective amount of balsalazide. Balsalazide and a pharmaceutically acceptable carrier or diluent, wherein the composition is formulated for treating a subject suffering from or susceptible to a bowel disorder, and packaged with instructions to treat a subject suffering from or susceptible to a bowel disorder.

Prescribing Information

A subject being administered balsalazide may be informed of one or more of the following:

GIAZO, film-coated tablets containing 1.1 g balsalazide, is indicated for the treatment of mildly to moderately active ulcerative colitis in male patients 18 years of age and older; effectiveness in female patients was not demonstrated in clinical studies. Safety and effectiveness of GIAZO therapy beyond 8 weeks have not been established.

For treatment of active ulcerative colitis in adult male patients, the usual dose is three 1.1 g GIAZO tablets to be taken 2 times a day with food (6.6 g per day) for up to 8 weeks.

GIAZO is available as yellow, oval, film-coated tablets containing 1.1 g balsalazide disodium, with BZT debossed on one side of the tablet.

GIAZO is contraindicated in patients with hypersensitivity to salicylates, balsalazide, or their metabolites, or to any of the components of GIAZO tablets. Hypersensitivity reactions may include, but are not limited to the following: anaphylaxis, bronchospasm, and skin reaction.

Mesalamine has been associated with an acute intolerance syndrome that may be difficult to distinguish from an exacerbation of ulcerative colitis. In controlled clinical studies with GIAZO in adults with ulcerative colitis, 7% of male patients reported exacerbation of the symptoms of ulcerative colitis. Symptoms include cramping, acute abdominal pain and bloody diarrhea, sometimes fever, headache, and rash. Observe patients closely for worsening of these symptoms while on treatment. If acute intolerance syndrome is suspected, promptly discontinue treatment with GIAZO.

Renal impairment, including minimal change nephropathy, acute and chronic interstitial nephritis, and, rarely, renal failure, has been reported in patients given products that release mesalamine in the gastrointestinal tract. It is recommended that patients have an evaluation of renal function prior to initiation of GIAZO therapy and periodically while on therapy. Exercise caution when using GIAZO in patients with known renal dysfunction or a history of renal disease.

There have been reports of hepatic failure in patients with pre-existing liver disease who have been administered mesalamine. Because balsalazide is converted to mesalamine, caution should be exercised when administering GIAZO to patients with liver disease.

Patients with pyloric stenosis may have prolonged gastric retention of GIAZO tablets, which may delay delivery of GIAZO to the colon.

Because clinical studies are conducted under widely varying conditions, adverse reaction rates observed in the clinical studies of a drug cannot be directly compared to rates in the clinical studies of another drug and may not reflect the rates observed in practice.

In an in vitro study using human liver microsomes, balsalazide and its metabolites [5-aminosalicylic acid (5-ASA), N-acetyl-5-aminosalyicylic acid (N-Ac-5-ASA), 4-aminobenzoyl-β-alanine (4-ABA), and N-acetyl-4-aminobenzoyl-β-alanine (N-Ac-4-ABA)] were not shown to inhibit the major CYP enzymes evaluated (CYP1A2, CYP2C9, CYP2C19, CYP2D6, and CYP3A4/5). Therefore, balsalazide and its metabolites are not expected to inhibit the metabolism of other drugs that are substrates of CYP1A2, CYP2C9, CYP2C19, CYP2D6, or CYP3A4/5.

Pregnancy Category B. Reproduction studies were performed in rats and rabbits at oral doses up to 2 g/kg/day, 2.5 and 4.9 times the recommended human dose based on body surface area for the rat and rabbit, respectively, and revealed no evidence of impaired fertility or harm to the fetus due to balsalazide disodium. There are, however, no adequate and well-controlled studies in pregnant women. Because animal reproduction studies are not always predictive of human response, this drug should be used during pregnancy only if clearly needed.

Mesalamine is known to cross the placental barrier.

It is not known whether balsalazide disodium or its metabolites are excreted in human milk. Because many drugs are excreted in human milk, caution should be exercised when GIAZO is administered to a nursing woman.

This invention is further illustrated by the following examples which should not be construed as limiting. The contents of all references, patents and published patent applications cited throughout this application are hereby incorporated by reference.

EXAMPLES

Example 1

Clinical Studies

The data described below reflect exposure of GIAZO in 565 ulcerative colitis patients with mildly to moderately active disease. GIAZO was evaluated in one placebo-controlled study (168 treated with GIAZO), one active-controlled study (210 treated with GIAZO); a subset of these patients also participated in an uncontrolled, open-label, extension study (additional 187 treated with GIAZO). The population studied had a mean age of 43.1 (range: 18-80) years; approximately 94% of patients were <65 years old, 49% were male, and 84% were white.

Adverse Reactions/Contraindications

In the placebo-controlled study, a greater proportion of patients experienced an adverse reaction in the placebo group (68%) compared with the GIAZO group (55%). The most common adverse reactions with GIAZO in male patients were headache, nasopharyngitis, anemia, diarrhea, fatigue, pharyngolaryngeal pain, and urinary tract infection. A lower proportion of GIAZO (10%) patients discontinued treatment due to an adverse reaction compared to the placebo group (13%). The majority of adverse reactions were mild to moderate in severity. The percentage of patients who experienced a serious adverse reaction was greater in the placebo group (5.1%) than the GIAZO group (2.4%). The most common serious adverse reactions were gastrointestinal disorders, which were mainly associated with symptoms of ulcerative colitis.

Adverse reactions occurring in at least 2% of male patients in the placebo-controlled study are listed in Table 1.

TABLE 1

Adverse Reactions Experienced by at Least 2% of GIAZO - Treated Male Patients and at a Rate Greater than Placebo in a Placebo-Controlled Phase 3 Study

| Adverse Reaction | GIAZO 6.6 g/day N = 82 | PLACEBO N = 37 |
|---|---|---|
| Anemia | 3.7% | 0% |
| Diarrhea | 3.7% | 0% |
| Pharyngolaryngeal Pain | 3.7% | 0% |
| Urinary Tract Infection | 3.7% | 0% |

TABLE 1-continued

Adverse Reactions Experienced by at Least 2% of GIAZO - Treated Male Patients and at a Rate Greater than Placebo in a Placebo-Controlled Phase 3 Study

| Adverse Reaction | GIAZO 6.6 g/day N = 82 | PLACEBO N = 37 |
|---|---|---|
| Arthralgia | 2.4% | 0% |
| Insomnia | 2.4% | 0% |
| Pain | 2.4% | 0% |

Data collected from all three studies (placebo-controlled, active-controlled, and open-label) showed that female patients reported adverse reactions more frequently than did male patients (76% and 66%, respectively).

The following adverse reactions, presented by body system, were reported infrequently (less than 1%) by GIAZO-treated ulcerative colitis patients in controlled studies.

Cardiovascular and Vascular: increased blood pressure, increased heart rate

Dermatological: erythema nodosum, rash

Gastrointestinal Disorders: abdominal pain, constipation, defecation urgency, diarrhea, dry mouth, hard feces, flatulence, gastroesophageal reflux disease, vomiting Hepatobiliary Disorders: increased aspartate aminotransferase Infections and Infestations: gastroenteritis, upper respiratory infection Musculoskeletal and Connective Tissue Disorders: arthralgia, back pain, myalgia Nervous System Disorders: dizziness, lethargy Respiratory, Thoracic and Mediastinal Disorders: dyspnea General Disorders and Administrative Site Disorders: face edema, fatigue, malaise, pain, pyrexia, swelling Because these reactions are reported voluntarily from a population of unknown size, it is not always possible to reliably estimate their frequency or establish a causal relationship to drug exposure. These adverse reactions have been chosen for inclusion due to a combination of seriousness, frequency of reporting, or potential causal connection to mesalamine.

The following adverse reactions have been identified during use of balsalazide-containing products in clinical practice:

Cardiovascular and Vascular: myocarditis, pericarditis, vasculitis

Dermatological: alopecia, pruritus

Gastrointestinal: pancreatitis

Respiratory: alveolitis, pleural effusion, pneumonia (with and without eosinophilia)

Renal: interstitial nephritis, renal failure

The following additional adverse reactions have been identified during post-approval use in clinical practice of products which contain (or are metabolized to) mesalamine:

Hepatobiliary Disorders: elevated liver enzymes (AST, ALT, GGT, LDH, alkaline phosphatase), elevated bilirubin, jaundice, cholestatic jaundice, cirrhosis, hepatocellular damage including liver necrosis and liver failure, Kawasaki-like syndrome including hepatic dysfunction. Some of these cases were fatal.

Absorption

After single-dose administration of 3.3 g GIAZO in 18 healthy subjects, the median time of peak plasma concentration ($T_{max}$) was 0.5 hr for balsalazide, while the median $T_{max}$ was 12 hr for both 5-ASA and N-Ac-5-ASA (Table 2). Pharmacokinetic parameters exhibited high variability, with % CV ranging from 31% to 67% for AUC and from 27% to 68% for $C_{max}$.

After repeated doses of 3.3 g GIAZO tablets every 12 hours, steady-state was achieved after about 3 days for balsalazide and all metabolites. The AUC and $C_{max}$ were the highest for N-Ac-5-ASA, followed by 5-ASA and balsalazide. There was minimal accumulation of balsalazide, as suggested by a 1.2-fold increase in AUC. On the other hand, a larger increase in the systemic exposure to metabolites was observed at steady-state. The accumulation ratios based on AUC for the metabolites were 6.1 for 5-ASA, 3.6 for N-Ac-5-ASA, 4.8 for 4-ABA, and 3.6 for N-Ac-4-ABA.

TABLE 2

Pharmacokinetic Parameters for Balsalazide and Metabolites (5-ASA and N-Ac-5-ASA) Following Single- and Repeated-Doses (Q12) of 3.3 g Balsalazide Disodium as GIAZO (N = 18)

| | Single Dose | | Repeated Dose | |
|---|---|---|---|---|
| Parameter | Mean | SD | Mean | SD |
| $C_{max}$ (mcg/mL) | | | | |
| Balsalazide | 0.3 | 0.2 | 0.3 | 0.2 |
| 5-ASA | 0.5 | 0.3 | 1.5 | 0.6 |
| N-Ac-5-ASA | 1.2 | 0.4 | 2.2 | 0.6 |
| $T_{max}{}^a$ (hours) | | | | |
| Balsalazide | 0.5 | (0.5-2) | 0.5 | (0.5-2) |
| 5-ASA | 12 | (8-16) | 12 | (1.5-16) |
| N-Ac-5-ASA | 12 | (8-16) | 10 | (1-16) |
| $AUC_{tau}$ (mcg · h/mL) | | | | |
| Balsalazide | 1.3 | 0.7 | 1.6 | 0.9 |
| 5-ASA | 2.2 | 1.6 | 13.4 | 6.3 |
| N-Ac-5-ASA | 5.9 | 2.9 | 21 | 6.4 |
| $AUC_{0-\infty}$ (mcg · h/mL) | | | | |
| Balsalazide | 1.4 | 0.8 | NA | NA |
| 5-ASA | 8.5 | 3.9 | NA | NA |
| N-Ac-5-ASA | 33.5 | 14.1 | NA | NA |
| $T_{1/2}{}^b$ (hour) | | | | |
| Balsalazide | 1.9 | 0.7 | 8.4 | 12.4 |
| 5-ASA | $9.5^b$ | 10.1 | 9.0 | 8.6 |
| N-Ac-5-ASA | $10.4^b$ | 17.6 | 7.2 | 6.8 |

$^a$Expressed as median and range.
$^b$N = 17.

Food Effect

After administration of single dose of 3.3 g (3×1.1 g tablets) of GIAZO with a high-fat meal, the AUC of balsalazide was unaffected compared to fasted administration, but the presence of food reduced both peak concentrations and AUC of the metabolites 5-ASA and N-Ac-5-ASA. A high fat meal increased the median $T_{max}$ for balsalazide from 0.5 to 2 hours; for 5-ASA from 12 to 24 hours; and for N-Ac-5-ASA from 12 to 24 hours. Under fed conditions, the mean $C_{max}$ was reduced by 44% for balsalazide, 65% for 5-ASA, and 48% for N-Ac-5-ASA. No significant changes were observed for $AUC_{0-\infty}$ for balsalazide; however, $AUC_{0-\infty}$ was reduced for 5-ASA by 46% and for N-Ac-5-ASA by 17%.

The binding of balsalazide to human plasma proteins was $\geq 99\%$; 5-ASA and N-Ac-5-ASA were 43% and 78% bound, respectively, to plasma proteins.

Following oral administration, balsalazide is cleaved by bacterial azoreduction to release equimolar quantities of 5-ASA, the active moiety, and 4-ABA, a carrier moiety. Mesalamine (5-ASA) and 4-ABA are further acetylated to N-Ac-5-ASA and N-Ac-4-ABA, respectively in the intestinal mucosa and liver. The terminal half-life was 1.9 h for balsalazide, 9.5 h for 5-ASA, and 10.5 h for N-Ac-5-ASA.

At steady-state following administration of repeated doses of 3.3 g GIAZO every 12 hours in healthy volunteers, the combined % of dose excreted in urine for balsalazide and its metabolites over 12 hours was 23%. The mean % of dose excreted in urine over 12 hours was 0.16% for balsalazide, 4.6% for 5-ASA, 15.6% for N-Ac-5-ASA, 0.40% for 4-ABA, and 1.8% for N-Ac-4-ABA.

Example 2

Carcinogenicity Studies

In a 24-month rat (Sprague Dawley) carcinogenicity study, oral (dietary) balsalazide disodium at doses up to 2 g/kg/day was not tumorigenic. For a 50 kg person of average height this dose represents 2.5 times the recommended human dose on a body surface area basis. Balsalazide disodium was not genotoxic in the following in vitro or in vivo tests: Ames test, human lymphocyte chromosomal aberration test, and mouse lymphoma cell (L5178Y/TK+/−) forward mutation test, or mouse micronucleus test. However, it was genotoxic in the in vitro Chinese hamster lung cell (CH V79/HGPRT) forward mutation test.

The compound 4-aminobenzoyl-β-alanine, a metabolite of balsalazide disodium, was not genotoxic in the Ames test and the mouse lymphoma cell (L5178Y/TK+/−) forward mutation test but was positive in the human lymphocyte chromosomal aberration test. N-acetyl-4-aminobenzoyl-β-alanine, a conjugated metabolite of balsalazide disodium, was not genotoxic in Ames test, the mouse lymphoma cell (L5178Y/TK+/−) forward mutation test, or the human lymphocyte chromosomal aberration test. Balsalazide disodium at oral doses up to 2 g/kg/day, 2.5 times the recommended human dose based on body surface area, was found to have no effect on fertility and reproductive performance in rats.

Example 3

Placebo-Controlled Study

A double-blind, placebo-controlled, multi-center study was conducted in 250 adult patients with mildly to moderately active ulcerative colitis. The study population was primarily white (84%), had a mean age of 44 years (7% age 65 years or older), and 49% were men. Disease activity was assessed using a modified Mayo Disease Activity Index[1] (MMDAI), which was a sum of four subscores (bowel frequency, rectal bleeding, endoscopic appearance, and physician's global assessment), each ranging from 0 to 3, with higher scores indicating worse disease. The median baseline MMDAI score was 8. Patients were randomized 2:1 to receive 8 weeks of treatment with either GIAZO 3.3 g twice daily or placebo.

The primary efficacy endpoint was to compare the proportion of patients that achieved clinical improvement and improvement in the rectal bleeding subscale of the MMDAI at the end of 8 weeks of treatment for GIAZO vs. placebo. Clinical Improvement was defined as having both a ≧3 point improvement from baseline in the MMDAI score and a ≧1 point improvement from baseline in the rectal bleeding subscore. Two key secondary efficacy endpoints compared the proportion of patients with Clinical Remission and Mucosal Healing at the end of 8 weeks of treatment for GIAZO vs. placebo. Clinical Remission was defined as a score of 0 for rectal bleeding and a combined score of ≦2 for bowel frequency and physician's assessment using the MMDAI sub-scale; the endoscopic sub-score was not considered in this definition. Mucosal Healing was defined as an endoscopy/sigmoidoscopy score of 0 or 1, where a score of 1 could include signs of erythema or decreased vascular pattern; by definition, the presence of friability indicated a score of 2 or 3.

After 8 weeks of treatment, the proportion of patients showing Clinical Improvement was greater for the GIAZO-treated group compared to the placebo group (Table 3).

TABLE 3

Proportion of Patients with Clinical Improvement* at Week 8 for the Total Population and by Gender Subgroups

|  | GIAZO | Placebo | p-value |
|---|---|---|---|
| Total Population | 55% | 40% | 0.0237 |
| Males | 57% | 20% |  |
| Females | 54% | 58% |  |

*Clinical Improvement: ≧3 improvement in MMDAI score and ≧1 point improvement in rectal bleeding.

These differences were statistically significant in the overall population; however, these effects were entirely driven by the results in the male subpopulation. With adjustment for multiplicity, statistically significant differences were also seen in the male patients for Clinical Remission (35% with GIAZO vs. 13% for placebo) and for Mucosal Healing (52% with GIAZO vs. 20% for placebo). Effectiveness of GIAZO was not demonstrated in the female subpopulation in the clinical trial.

Conclusions

Instruct patients not to take GIAZO if they have a hypersensitivity to salicylates (e.g., aspirin).

Instruct patients to take GIAZO with food.

Instruct patients to contact their health care provider if they experience a worsening of their ulcerative colitis symptoms, because it could be due to a reaction to GIAZO.

Instruct patients to make sure they let their health care provider know:

if they have or are later diagnosed with renal dysfunction. Damage to the kidney has been observed in some people given medications similar to GIAZO.

if they have or are later diagnosed with liver disease. Worsening liver disease has been observed in some people given medications similar to GIAZO.

if they have or are later diagnosed with pyloric stenosis, because GIAZO tablets may be slow to pass through their digestive tract.

Incorporation by Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a gastrointestinal disorder in a male subject comprising administering to the male subject in need of treatment a therapeutically effective amount of balsalazide.

2. The method claim 1, wherein the therapeutically effective amount comprises about 6.5 to about 6.8 g per day.

3. The method claim 1, wherein the therapeutically effective amount comprises about 6.6 g per day.

4. The method claim 1, wherein the therapeutically effective amount comprises about 6.75 g per day.

5. The method of claim 1, wherein the therapeutically effective amount is a dosage regimen of three tablets of the formulation two times each day, wherein each tablet comprises about 1100 mg of balsalazide.

6. The method of claim 5, wherein the balsalazide tablet is a film-coated tablet.

7. The method of claim 1, wherein the therapeutically effective amount is a dosage regimen of three capsules of the formulation three times each day, wherein each capsule comprises about 750 mg of balsalazide.

8. The method of claim 1, wherein the administration to the subject occurs between about 30 minutes prior to about 1 hour after consuming food.

9. The method of claim 1, wherein the gastrointestinal disorder comprises ulcerative colitis.

10. The method of claim 9, wherein the ulcerative colitis is mild to moderately active ulcerative colitis.

11. A method of decreasing a MMDAI score in a male subject having ulcerative colitis comprising administering to the male subject a therapeutically effective amount of balsalazide, thereby decreasing the MMDAI score.

12. The method claim 11, wherein the therapeutically effective amount comprises between about 6.5 to about 6.8 g per day.

13. The method claim 11, wherein the therapeutically effective amount comprises about 6.6 g per day.

14. The method claim 11, wherein the therapeutically effective amount comprises about 6.75 g per day.

15. The method of claim 12, wherein the therapeutically effective amount is a dosage regimen of three tablets of the formulation two times each day, wherein each tablet comprises about 1100 mg of balsalazide.

16. The method of claim 15, wherein the balsalazide tablet is a film-coated tablet.

17. The method of claim 11, wherein the therapeutically effective amount is a dosage regimen of three capsules of the formulation three times each day, wherein each capsule comprises about 750 mg of balsalazide.

18. The method of claim 11, wherein the MMDAI score is decreased by 3 or more points.

19. The method of claim 11, wherein the rectal bleeding component of the MMDAI score is decreased by 1 or more points.

20. A method of inducing clinical remission of ulcerative colitis in a male subject comprising administering to the male subject a therapeutically effective amount of balsalazide, thereby inducing remission in the subject.

21. The method claim 20, wherein the therapeutically effective amount comprises between about 6.5 to about 6.8 g per day.

22. The method claim 20, wherein the therapeutically effective amount comprises about 6.6 g per day.

23. The method claim 20, wherein the therapeutically effective amount comprises about 6.75 g per day.

24. The method of claim 21, wherein the therapeutically effective amount is a dosage regimen of three tablets of the formulation two times each day, wherein each tablet comprises about 1100 mg of balsalazide.

25. The method of claim 24, wherein the balsalazide tablet is a film-coated tablet.

26. The method of claim 20, wherein the therapeutically effective amount is a dosage regimen of three capsules of the formulation three times each day, wherein each capsule comprises about 750 mg of balsalazide.

27. The method of claim 20, wherein remission is defined by MMDAI component scores of zero for rectal bleeding and a combined score of 2 or less for bowel frequency and physician's assessment.

28. A method of inducing mucosal healing in a male subject having ulcerative colitis comprising administering to the male subject a therapeutically effective amount of balsalazide, thereby inducing mucosal healing in the subject.

29. The method claim 28, wherein the therapeutically effective amount comprises between about 6.5 to about 6.8 g per day.

30. The method claim 28, wherein the therapeutically effective amount comprises about 6.6 g per day.

31. The method claim 28, wherein the therapeutically effective amount comprises about 6.75 g per day.

32. The method of claim 29, wherein the therapeutically effective amount is a dosage regimen of three tablets of the formulation two times each day, wherein each tablet comprises about 1100 mg of balsalazide.

33. The method of claim 32, wherein the balsalazide tablet is a film-coated tablet.

34. The method of claim 28, wherein the therapeutically effective amount is a dosage regimen of three capsules of the formulation three times each day, wherein each capsule comprises about 750 mg of balsalazide.

35. The method of claim 28, wherein the mucosal healing is defined as an improvement in endoscopy/sigmoidoscopy score to 0 or 1.

* * * * *